United States Patent
Tange

(10) Patent No.: US 6,736,917 B2
(45) Date of Patent: May 18, 2004

(54) PROCESS FOR MANUFACTURING ELASTICALLY STRETCHABLE AND CONTRACTIBLE COMPOSITE SHEET

(75) Inventor: Satoru Tange, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

(21) Appl. No.: 09/944,476

(22) Filed: Aug. 31, 2001

(65) Prior Publication Data

US 2002/0023710 A1 Feb. 28, 2002

(30) Foreign Application Priority Data

Aug. 31, 2000 (JP) .......................... 2000-262656

(51) Int. Cl.[7] .............. D06C 3/06; B32B 31/08; B29C 65/00; B65C 9/25
(52) U.S. Cl. ............. 156/181; 156/182; 156/229; 156/290; 156/306.6; 156/324; 428/198; 428/365; 28/172.2
(58) Field of Search .................. 156/73.4, 163, 156/165, 181, 182, 184, 197, 199, 229, 272.2, 290, 306.6, 308.6, 324; 28/172.2; 428/198, 365, 374, 148

(56) References Cited

U.S. PATENT DOCUMENTS

| | | | | | |
|---|---|---|---|---|---|
| 2,867,560 | A | * | 1/1959 | Strawinski | .............. 156/229 |
| 5,683,787 | A | * | 11/1997 | Boich et al. | ............... 156/163 |
| 6,217,692 | B1 | * | 4/2001 | Kling | ................... 156/229 |
| 6,361,527 | B1 | * | 3/2002 | Van Gompel et al. | ...... 108/158 |

FOREIGN PATENT DOCUMENTS

| | | | | |
|---|---|---|---|---|
| JP | 8-504693 | | 5/1996 | |
| WO | WO 9519258 A1 | * | 7/1995 | .......... B32B/3/10 |

* cited by examiner

Primary Examiner—Richard Crispino
Assistant Examiner—Sing P Chan
(74) Attorney, Agent, or Firm—Butzel Long

(57) ABSTRACT

A process for manufacturing a composite sheet by joining a second web made of thermoplastic synthetic fiber and capable of inelastic extension to at least one surface of a first web capable of elastic stretch and contraction in an intermittent manner. The process involves a step of extending the first web and a step of allowing the first web to retract, and a step of joining a second web to the second web while in a retracted state are included.

6 Claims, 2 Drawing Sheets

PROCESS FOR MANUFACTURING ELASTICALLY STRETCHABLE AND CONTRACTIBLE COMPOSITE SHEET

BACKGROUND OF THE INVENTION

The present invention relates to a process for manufacturing an elastically stretchable and contractible composite sheet comprising a web capable of elastic stretch and contraction and a fibrous web capable of inelastic extension.

Japanese Patent Publication No. 1996-504693A discloses a multi-layered elastic panel, as one example of this type of composite sheet, and a process of manufacturing the same. This manufacturing process of a multi-layered elastic panel involves arranging a rubber elastic layer and an inelastic fibrous layer, one over another, joining them intermittently, extending the combination up to the vicinity of a breaking extension limit of the inelastic fibrous layer and finally relaxing the combination from tension.

In the composite sheet (elastic panel) obtained via the above-specified known manufacturing process, the rubber elastic layer after removal of the tension is unable to return to its original dimension. The resulting difference in dimension sometimes produces a permanent strain in the composite sheet. Such a permanent strain is a first factor that makes the composite sheet larger in dimension along a direction of extension than before it is extended. Also, the inelastic fibrous layer when extended undergoes plastic deformation so that its dimension after extension is made larger than before extension. When the rubber layer is released from the tension, this dimensional difference causes the inelastic fibrous layer to increase its apparent bulk. The increased bulk then becomes a second factor that makes the composite sheet larger in dimension than before extension by restraining the rubber elastic layer from recovering, i.e., by restricting elastic contraction thereof. By these first and second factors, the composite sheet when again extended to the vicinity of a breaking extension limit of the inelastic fibrous layer exhibits a lower percentage extension than when initially extended to the vicinity of the breaking extension limit of the inelastic fibrous layer.

SUMMARY OF THE INVENTION

It is an object of the present invention to provide a process for manufacturing a composite sheet which can reduce the influence of the above-described first factor encountered in the known manufacturing process and thus widen the range that permits elastic stretch and contraction of the sheet.

To achieve this object, the present invention is directed to a process for manufacturing a composite sheet capable of elastic stretch and contract in one direction, which includes the steps of continuously feeding a first web capable of elastic stretch and contraction in the one direction and having a top surface and a bottom surface, continuously feeding a second web capable of inelastic extension and composed of thermoplastic synthetic fibers on at least one surface of the first web and joining the first and second webs in an intermittent manner along the one direction.

In the above-described manufacturing process of the composite sheet, the present involves the steps of:

(a) feeding the first web continuously in the one direction and extending the first web in the one direction within the range that permits elastic stretch and contraction of the first web;

(b) allowing the extended first web to retract by the action of an elastic contraction force of the web; and (c) superimposing the second web on at least one surface of the first web after retraction and joining the first and second webs in an intermittent manner along the one direction.

In one embodiment of this invention, subsequent to the step (c), the following steps are further included:

(d) a secondary extension step wherein the joined first and second webs are extended in the one direction within the range that permits elastic stretch and contraction of the first web; and (e) a secondary contraction step wherein the extended first and second webs are allowed to retract by the action of an elastic contraction force of the first web.

DETAILED DESCRIPTION OF THE PREFERRED EMBODIMENTS

The process for manufacturing an elastically stretchable and contractible composite sheet in accordance with the present invention is below described in detail with reference to the attached drawings.

Figure 1:
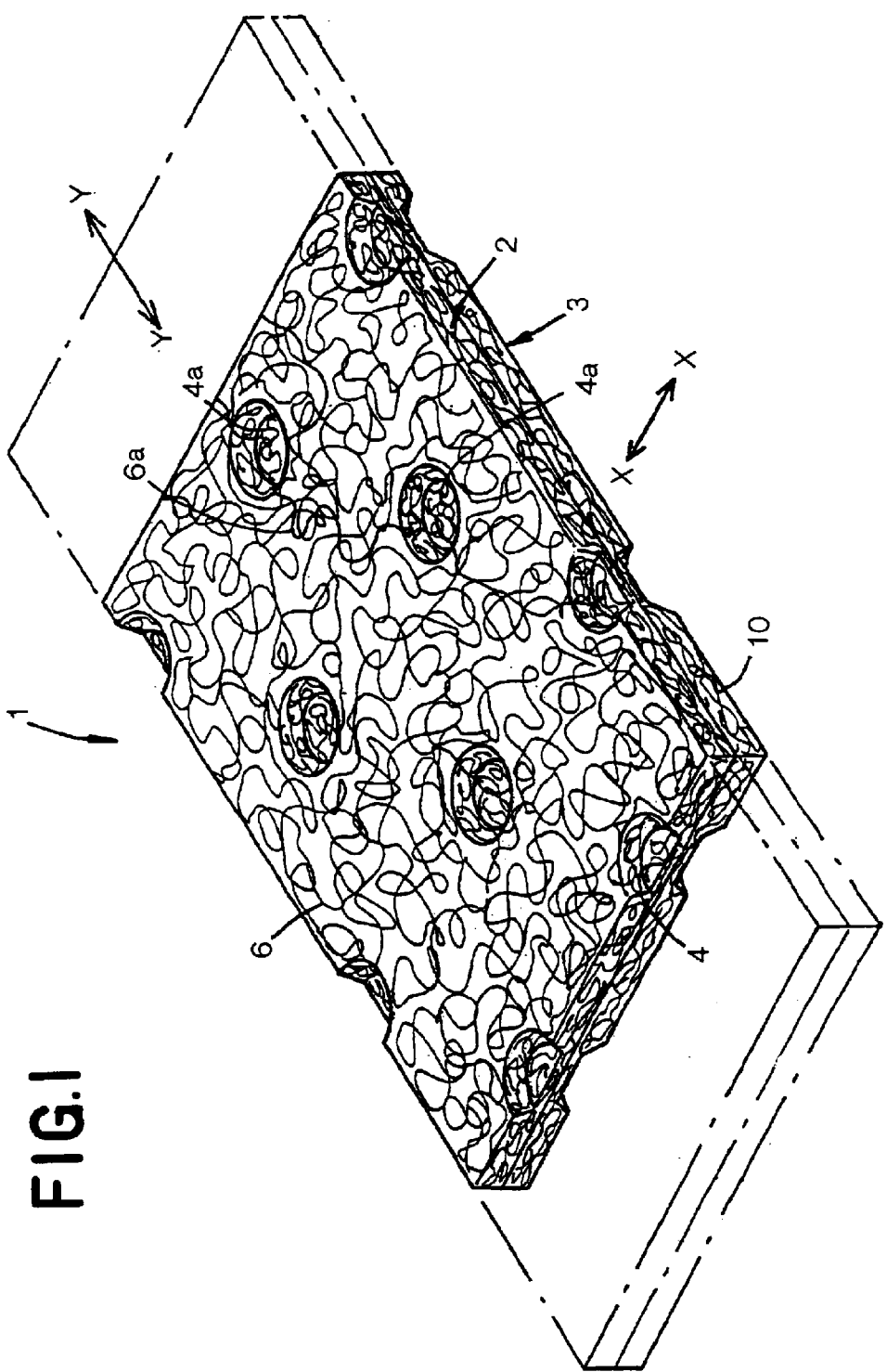
FIG. 1 is a perspective view of a composite sheet.

FIG. 1 is a perspective view of an elastically stretchable and contractible composite sheet 1 manufactured by the practice of the method according to the present invention.

The composite sheet 1 is suitable for use as a liquid permeable or impermeable facing material of a disposable wearing article such as a disposable diaper, a sanitary napkin, a disposable medical gown or the like, and has an upper layer 2 and a lower layer 3 united together at bond areas 4 by fusion. The composite sheet 1 is elastically stretchable and contractible at least in the Y—Y direction, out of mutually-perpendicular double-headed arrows X—X and Y—Y, as shown by chain lines.

The upper layer 2 of the composite sheet 1 is capable of inelastic extension at least in the Y—Y direction, out of the X—X and Y—Y directions. Such the upper layer 2 comprises a mass of thermoplastic synthetic fibers extending continuously between bond areas 4 and 4, preferably long fibers, more preferably a mass of continuous fibers 6. In the preferred upper layer 2, the fibers 6 are fused to each other at bond areas 4 but are individualized between bond areas 4 such that they are neither fused nor mechanically entangled tightly with each other. The length of a portion of the individual fiber 6 that extends between adjacent bond areas 4, e.g., the length of a portion of the fiber 6a that extends between bond areas 4a and 4a is larger than a linear distance between the bond areas 4a and 4a. That is, the fiber 6 extends over an upper surface of the lower layer 3 while describing the shown irregular curves. When the composite sheet is extended in the Y—Y direction, the fibers 6 change their orientations between the bond areas 4 and 4 to extend linearly along the Y—Y direction. As the composite sheet 1 retracts, the fibers 6 describe curves again.

The lower layer 3 of the composite sheet 1 is elastically stretchable and contractible in the Y—Y direction, preferably in both the X—X and Y—Y directions. The lower layer 3 comprises a mass of short, long or continuous fibers made of elastic materials such as thermoplastic elastomers, or alternatively, comprises a film or the like made of such elastic materials. In the case of fibers, the lower layer takes the form of a non-woven or woven fabric, preferably integrated via mechanical entanglement or fusion bond of fibers. The lower layer 3 operates such that it extends elastically as the composite sheet 1 is extended in the Y—Y direction by an external force and causes the composite sheet 1 to retract as the composite sheet 1 is freed from the force.

Figure 2:
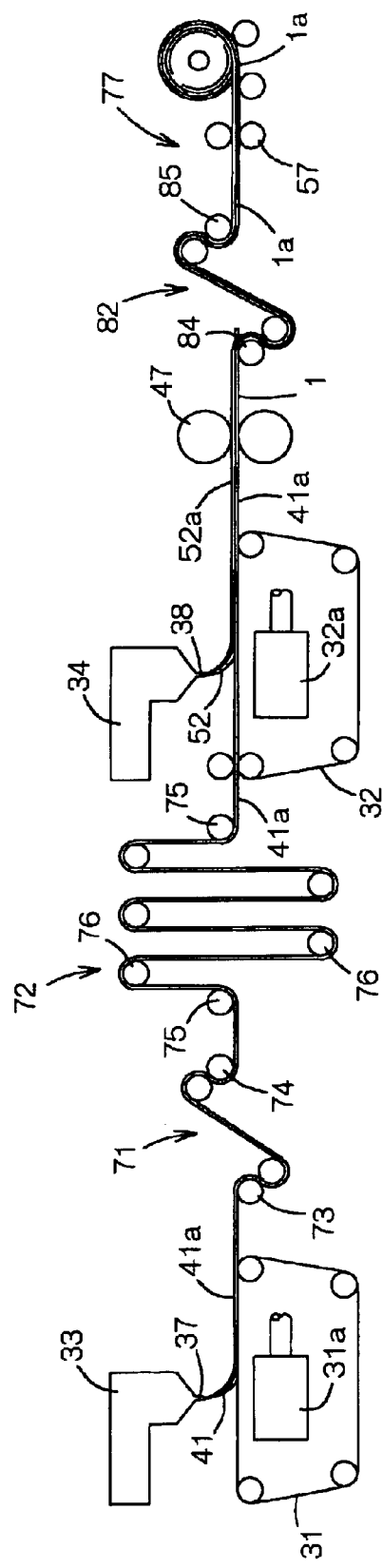
FIG. 2 is a view showing an exemplary process for manufacturing the composite sheet.

FIG. 2 is a diagram illustrating a manufacturing process of the composite sheet 1 shown in FIG. 1. On the left side of the drawing, a first endless belt 31 and a second endless belt 32 which both run toward the right are juxtaposed to interpose a first extension step 71 and a first contraction step 72 therebetween. A first extruder 33 and a second extruder 34 are disposed over the endless belts 31 and 32, respectively. The extruder 33, 34 has a plurality of nozzles 37, 38 arranged in a row and transverse direction to the endless belt 31, 32. A suction duct 31a, 32a is disposed right under the extruder 33, 34 through the endless belt 31, 32. The first extension step 71 involves a pair of first rolls 73 and a pair of second rolls 74. The second roll 74 rotates at a faster speed than the first roll 73. The first contraction step 72 involves a plurality of third rolls 76 arranged substantially in a machine direction. The foremost third roll 76 rotates at a peripheral speed close to that of the second roll 74, the following third rolls 76 rotate at peripheral speeds slowed in the sequence toward the rear, and the rearmost third roll is controlled to coincide in peripheral speed with the first roll 73. A guide roll 75 is provided in both front and rear sides of the first contraction step 72.

Plural streams of first continuous fibers 41, made of a thermoplastic elastomer and capable of elastic stretch and contraction, are discharged from the nozzles 37 of the first extruder 33 and directed onto the first endless belt 31 under the suction action of the duct 31a. The first continuous fibers 41 are preferably fused to each other over the first endless belt 31 and rendered into a first web 41a having the form of a non-woven fabric. The first web 41a is conveyed in a machine direction and then extended in the machine direction at a specific extension ratio as required. The first web 41a advances to the first contraction step 72 where it is released from the tension and allowed to retract while passing through the third rolls 76 arranged in a sequence of decreasing peripheral speed. The first web 41a subsequent to retraction advances toward the second endless belt 32. Plural streams of second continuous fibers 52, made of a thermoplastic synthetic resin and capable of inelastic extension, are discharged from the nozzles 38 of the second extruder 34 and directed onto the first web 41a under the suction action of the duct 32a to form a second web 52a.

The superimposed first and second webs 41a and 52a are brought between a pair of hot emboss rolls 47 and united together by fusion at bond areas 4 (see FIG. 1) arranged at intervals in the machine direction to form a composite sheet 1 shown in FIG. 1.

The composite sheet 1 can be controlled to further advance in the machine direction and treated into a second composite sheet 1a. A next step that follows in the machine direction is a second extension step 82, involving a pair of fourth rolls 84 and a pair of fifth rolls 85, in which the composite sheet 1 is extended in the machine direction at a specific extension ratio as required. In the second extension step 82, the fifth roll 85 rotates with a faster peripheral speed than the fourth roll 84. After passage between the fifth rolls 85, the composite sheet 1 advances to enter between a pair of carrying rolls 57 which rotate with almost the same peripheral speed as the first rolls 73. The composite sheet 1 extended in the second extension steps 82 is released from tension in the second contraction step 82 involving the fifth rolls 85 and the carrying rolls 57, allowed to retracts by the action of an elastic recovery force of the first web 41a, and then wound round a roll as the second composite sheet 1a. The composite sheet 1 shown in FIG. 1, when subjected to a single cycle of extension and contraction, results in the second composite sheet 1a which is applicable for the similar uses as the composite sheet 1.

In the above-described manufacturing process of the composite sheet 1, SEPS or the like may be used, for example, for the thermoplastic elastomer which is raw material of the first continuous fibers 41. The use of first continuous fibers 41 having a fiber diameter of 18 $\mu$m results in the first web 41a having a basis weight of 31.9 g/m$^2$. This first web 41a has a machine-direction breaking strength of 2.35 N per width of 50 mm and a breaking extension of 447%. In the first extension steps 71, the extension ratio is within the range that permits elastic stretch and contraction of the first web 41a and within a breaking extension of the second web 52a. For example, a 100 mm length of the first web 41a can be extended in the first extension step 71 by 120% of its original length, i.e., to a length of 220 mm. This is allowed to retract in the first contraction step 72 to a length of 113.5 mm. That is, when the first web 41a is extended by 120% of its original length, a permanent strain of 13.5 mm (13.5%) is produced per 100 mm of the first web 41a. This permanent strain is conceivably attributed to the rearrangement of the first continuous fibers 41 in the first web 41a. Such a permanent strain is generally reduced if the first web 41a is in the form of an elastic film.

Examples of thermoplastic synthetic resins for use as raw material of the second continuous fibers 52 include polypropylene; a 60:40 (by weight) mixture of polypropylene and a terpolymer of propylene, ethylene and butene; polyester; polyethylene and the like. As an example, the aforementioned mixture of polypropylene and terpolymer can be used to form the second continuous fibers 52 having a diameter of 17.5 $\mu$m and a percentage extension of 311% and then form the second web 52a having a basis weight of 15.0 g/m$^2$ from such fibers 52.

To illustrate the case where this second web 52a is joined to the aforementioned first web 41a obtained via extension by 120% and subsequent contraction and measuring a length of 113.5 mm to provide the composite sheet 1, extension of the composite sheet 1 by 100% in the second extension step 82 and subsequent contraction in the second contraction step 77 results in the second composite sheet 1a which shows an elastic recovery of 93%, out of 100% extension, and a remaining permanent strain of 7%.

For the purposes of comparison to this composite sheet 1, a prior art elastic panel was obtained by joining the 113.5 mm long first web 41a before subjected to the first extension to the 113.5 mm long second web 52b. The elastic panel was extended by 100% and then allowed to retract. The elastic recovery was 80% and 20% remained as a permanent strain. The increased permanent strain remained in the elastic panel than in the composite sheet 1. As clear from the comparison, the composite sheet 1 exhibits the superior elastic recovery, higher elastic extension and wider range of elastic extension and contraction, compared to the prior art elastic panel.

In the manufacturing process in accordance with this invention, the second web 52a capable of inelastic extension is used having a breaking extension of 40% or higher, preferably 70% or higher, more preferably 100% or higher, at least in the machine direction, out of the machine and cross directions. The first web 41a capable of elastic stretch and contraction preferably has a breaking extension higher than that of the second web 52a. More preferably, the first web 41a sustains its ability to elastically stretch and contract even at the breaking extension of the second web 52a. The composite sheet 1, if constructed from such first and second webs 41a and 52a, can be extended up to the vicinity of the breaking extension limit of the second web 52a. In the case where the continuous fibers 52 forming the second web 52a are engaged with each other by mechanical entanglement or fusion bond thereof, it is preferred that fibers 52 are largely freed from the engagement and thereby individualized in the second extension step 76. This increases a bulk of the second web 52a as it retracts, so that the composite sheet 1 provides a softer skin contact.

In this invention, the composite sheet 1 can be rendered into a three-layer structure by placing the second web 52a on top and bottom surfaces of the first web 41a. In such a case, the second webs 52a, 52a joined to the top and bottom surfaces of the first web 41a may be of the same properties or made different from each other in any of the following properties; basis weight, density, type of the thermoplastic synthetic resin used to form the continuous fibers 52, fiber diameter and fiber length. The illustrated first and second continuous fibers 41, 52 may be altered to short fibers with a length of 50 mm or less, or to long fibers having a length in the approximate range of 50–300 mm.

In the manufacturing process of an elastically stretchable and contractible composite sheet in accordance with this invention, an elastically stretchable and contractible web obtained via a sequence of extension and contraction effective to remove a major proportion of permanent strain and a web capable of inelastic extension are superimposed on each other and then united together. Accordingly, the resulting composite sheet exhibits a wider range of elastic extension and contraction, compared to an elastic panel resulting from a conventional manufacturing process wherein a web capable of elastic extension and contraction and a web capable of inelastic extension are superimposed and then united together.

What is claimed is:

1. A process for manufacturing a composite sheet capable of elastic stretch and contract in one direction, said process including the steps of:

(a) providing a first web capable of elastic stretch and contraction and having a top surface and a bottom surface;

(b) continuously feeding the first web along one direction;

(c) extending the first web in the one direction within a range that permits elastic stretch and contraction of the first web;

(d) allowing the extending first web to retract by an elastic contraction force of the web;

(e) continuously feeding at least one second web along the one direction, said second web comprising a nonwoven fabric formed of fibers which are deposited in a layer without mechanical entanglement;

(f) superimposing said at least one second web on at least one of said top surface and said bottom surface of the first web after said first web has been extended and refracted in steps (c) and (d); and (g) joining the first and second webs in an intermittent manner along the one direction.

2. The process of claim 1 further including, subsequent to the step (f) the following steps:

(i) a secondary extension step wherein the joined first and second webs are extended in the one direction within a range that permits elastic stretch and contraction of the first web; and (ii) a secondary contraction step wherein the extended first and second webs are allowed to retract by action of an elastic contraction force of the first web.

3. The process of claim 2, wherein the second web comprises synthetic fibers which are initially engaged with each other by at least one of mechanical entanglement and fusion bonding and, subsequently in the step (e) the thermoplastic synthetic fibers are disengaged so that they are individualized.

4. The process of claim 1 wherein the at least one second web comprises two second webs with the one second web joined to the top surface if the first web and another second web joined to the bottom surface of the first web, the second webs being distinguishable from each other by at least one property selected from the group consisting of basis weight, density, type of the thermoplastic resin, diameter, and length of the fibers thereof.

5. The process of claim 1 wherein said first web comprises at least one of a fabric capable of elastic stretch and contraction and composed of thermoplastic synthetic fibers, and a film capable of elastic stretch and contraction and made of a thermoplastic synthetic resin.

6. The process of claim 1 wherein said thermoplastic synthetic fibers in the second web comprise continuous fibers.

* * * * *